US005983131A

United States Patent [19]
Weaver et al.

[11] Patent Number: 5,983,131
[45] Date of Patent: Nov. 9, 1999

[54] APPARATUS AND METHOD FOR ELECTROPORATION OF TISSUE

[75] Inventors: James C. Weaver, Sudbury, Mass.; Uwe Pliquett, Bielefeld-Grossdornberg, Germany; Timothy Vaughan, Chestnut Hill, Mass.

[73] Assignee: Massachusetts Institute of Technology, Cambridge, Mass.

[21] Appl. No.: 08/695,032

[22] Filed: Aug. 9, 1996

Related U.S. Application Data

[60] Provisional application No. 60/002,210, Aug. 11, 1995.

[51] Int. Cl.⁶ ...................................................... A61N 1/30
[52] U.S. Cl. .......................... 604/20; 607/153; 435/173.6
[58] Field of Search ........ 604/20–21; 435/173.5–173.6; 607/153

[56] References Cited

U.S. PATENT DOCUMENTS

| | | | |
|---|---|---|---|
| 578,611 | 3/1897 | Rively | 704/21 |
| 3,078,850 | 2/1963 | Schein et al. | 128/419 |
| 3,215,139 | 11/1965 | Dietz . | |
| 3,614,955 | 10/1971 | Mirowski et al. . | |
| 3,680,544 | 8/1972 | Shinnick et al. | 128/2 R |
| 4,055,799 | 10/1977 | Coster et al. | 324/71 |
| 4,081,340 | 3/1978 | Zimmermann et al. | 204/180 |
| 4,154,668 | 5/1979 | Zimmermann et al. | 204/299 |
| 4,220,916 | 9/1980 | Zimmermann et al. | 324/71 |
| 4,411,648 | 10/1983 | Davis et al. | 604/21 |

(List continued on next page.)

FOREIGN PATENT DOCUMENTS

| | | | |
|---|---|---|---|
| 01011564 | 1/1989 | Japan | A61N 1/00 |
| 64-11564 | 1/1989 | Japan | A61N 1/00 |

OTHER PUBLICATIONS

Mir et al., "Pharmacological Applications of Electropermeaization of Living Cells", *Lab. De Biochimie–Enzymologie*, Institute Gustave–Roussy 94805 Villejuif Cadex—France.

Zewert et al., "Transdermal Transport of DNA Antisense Oligonucleotides by Electroporation", *Biochemical and Biophysical Research Communications* 212:286–292 (1995).

Scott et al., "Transport of Ionic Species in Skin: Contribution of Pores to the Overall Skin conductance", *Pharmaceutical Research* 10:1699–1709 (1993).

Mir et al., "Electrochemotheraph Potentiation of Antitumour Effect of Bleomycin by Local Electric Pulses", *Eur. F. Cancer* 27(1):68–72 (1991).

Okino et al., "Effects of a High–Voltage Electrical Impulse and an Anticancer Drug on In Vivo Growing Tumors", *Jpn. J. Cancer Res.* 78(12):1319–1321 (1987).

Heroux et al., "Assessment of Trauma in tissues By Electrica Impedance Measurements", *Electromagnetics in Biology and Medicine*, pp. 215–221 (1991).

(List continued on next page.)

*Primary Examiner*—Mark Bockelman
*Attorney, Agent, or Firm*—Hamilton, Brook, Smith & Reynolds, PC

[57] ABSTRACT

The present invention relates to an apparatus and method for localized electroporation of tissue. An apparatus includes a perforate electrically insulating layer, a first electrode at a first side of the perforate electrically insulating layer and a second electrode at a second side of the perforate electrically insulating layer. An electric field extending between the first and second electrodes will preferentially extend through perforations of the electrically insulating layer. The electric field thereby causes electroporation of tissue that is proximate to the first electrode and is partitioned from the electrically insulating layer and the second electrode by the first electrode. The apparatus controllably limits the depth of the electric field within a tissue, such as skin, thereby electroporating a surface layer, such as a stratum corneum layer of the skin, without stimulating submerged nerve endings within the skin. Sensation of the applied voltage and especially pain sensation can thereby be controlled by the invention.

20 Claims, 5 Drawing Sheets

U.S. PATENT DOCUMENTS

| | | | |
|---|---|---|---|
| 4,578,168 | 3/1986 | Hofmann | 204/299 |
| 4,663,292 | 5/1987 | Wong et al. | 435/287 |
| 4,695,547 | 9/1987 | Hilliard et al. | 435/173 |
| 4,764,473 | 8/1988 | Matschke et al. | 435/287 |
| 4,784,737 | 11/1988 | Ray et al. | 204/180 |
| 4,808,152 | 2/1989 | Sibalis . | |
| 4,822,470 | 4/1989 | Chang | 204/299 |
| 4,955,378 | 9/1990 | Grasso | 128/421 |
| 4,979,948 | 12/1990 | Geddes et al. | 606/33 |
| 5,002,527 | 3/1991 | Reller et al. . | |
| 5,007,995 | 4/1991 | Takahashi et al. | 204/299 |
| 5,019,034 | 5/1991 | Weaver et al. | 604/20 |
| 5,047,007 | 9/1991 | McNichols et al. | 604/20 |
| 5,087,240 | 2/1992 | Sibalis . | |
| 5,098,843 | 3/1992 | Calvin | 435/287 |
| 5,137,817 | 8/1992 | Busta et al. | 435/173 |
| 5,156,591 | 10/1992 | Gross et al. . | |
| 5,279,543 | 1/1994 | Glikfeld et al. | 604/20 |
| 5,296,222 | 3/1994 | Petersen et al. | 424/94 |
| 5,298,017 | 3/1994 | Theeuwes et al. | 604/20 |
| 5,383,848 | 1/1995 | Hillman et al. | 604/20 |
| 5,389,069 | 2/1995 | Weaver | 604/21 |
| 5,445,609 | 8/1995 | Latin et al. | 604/20 |
| 5,462,520 | 10/1995 | Hofmann et al. | 604/20 |
| 5,507,724 | 4/1996 | Hofmann et al. . | |
| 5,547,467 | 8/1996 | Pliquett et al. | 604/20 |
| B1 5,019,034 | 8/1995 | Weaver et al. | 604/20 |

OTHER PUBLICATIONS

Bhatt et al., "Rhabdomyolysis due to Pulsed Electric Fields" *Plastic and Reconstructive Surgery 86*(1):1–11 (1990).

Heller et al., "Transfer of Human Membrane Surface Components by Incorporating Human Cells into Intact Animal Tissue by Cell Tissue Electrofusion In Vivo", *Biochimica et Biophysica Acta 1024*:185–188 (1990).

Titomirov et al., "In Vivo Electroporation and Stable Transformation of Skin Cells of Newborn Mice by Plasmid DNA", *Biochimica et Biophysica Acta. 1088*:131–134 (1991).

Okino, et al., *Journal of Japan Soc. For Cancer Therapy 22*(8):337 (1987).

Kanesda, et al., *Journal of Japan Soc. For Cancer Therapy 22*(8):338 (1987).

Okino et al., *Japan Journal of Cancer Research 46*:420 (1987).

Weaver, "Electroporation: A General Phenomenon for Manipulating Cells and Tissues", *Journal of Cellular Biochemistry 51*:426–435 (1993).

Prausnitz et al., "Electroporation of mammalian skin: A mechanism to enhance transdermal drug delivery", *Proc. Natl. Acad. Sci. USA 90*:10504–10508 (1993).

Prausnitz et al., "Methods for in Vivo Tissue Electroporation Using Surface Electrodes", Academic Press, Inc. *Drug Delivery 1*:125–131 (1993).

Bergan et al., "Electroporation enhances c–myc antisense oligodeoxynucleotide efficacy", *Nucleic Acids Research 21*(15):3567–3573.

Zewert et al., "Transdermal Transport of DNA Antisense Oligonucleotides by Electroporation", *Biochemical and Biophysical Research Comm. 212*(2):286–292.

Zimmermann et al., "Effects of External Electrical Fields on Cell Membranes", *Bioelectrochemistry and Bioenergetics 3*:58–83 (1976).

Tamada et al., "Measurement of Glucose in Diabetic Subjects Using Noninvasive Transdermal Extraction", *Nature Medicine 1*:1198–1202 (1995).

Dinh et al., "Upper and Lower Limits of Human Skin Electrical Resistance in Iontophoresis", *American Institute of Chemical Engineers Joural 39*(12):2011–2018 (1993).

Pliquett et al., "Imaging of Fluorescent Molecules and Small Ion Transport Through Human Stratum Corneum During High–Voltage Pulsing: Localized Transport Regions are Involved", *J. Biophysical Chemistry 58*:185–204 (1996).

Pliquett et al., "Changes in the Passive Electrical Properties of Human Stratum Corneum Due to Electroporation", *Biochemica et Biophysica Acta 1239*:111–121 (1995).

Edwards et al., "Analysis of Enhanced Transdermal Transport by Skin Electroporation", *Journal of Controlled Release 34*:211–221 (1995).

APPARATUS AND METHOD FOR ELECTROPORATION OF TISSUE

RELATED APPLICATION

This is an application claiming priority to Provisional Application No. 60/002,210, filed on Aug. 11, 1995, the entire teachings of which are incorporated herein by reference.

GOVERNMENT FUNDING

This invention was made with Government support under Grant No. DAAL03-090-G-0218 awarded by the Department of the Army and NIH-5R01-GM34077, awarded by the National Institutes of Health. The Government has certain rights in the invention.

BACKGROUND OF THE INVENTION

Delivery and retrieval of molecules and ions contained in fluids into or through skin tissue is an accepted method for many types of therapeutic and diagnostic treatment. Generally, transfer of fluids through skin tissue is achieved by use of a hypodermic needle. However, use of hypodermic needles can be painful, and provide relatively little temporal control for drug delivery. Also, in the case of treating diseased tissue, the effect of chemical agents on the diseased tissue is often dependent upon delivery of the chemical agent across cell membranes of the cells in the tissue mass, as opposed to simply injecting the chemical agent into the tissue. Further, chemical agents which are injected into diseased tissue typically enter the bloodstream and are transported away from the targeted tissue mass before they have a significant therapeutic effect on the tissue mass into which they were injected. Also, there are many problems that are often associated with treatment of cells by conventional methods, such as by intravenous injection. For example, the cells of melanoma tumors are typically difficult to target by injection techniques because they are in the form of relatively thin tissue. Further, injections can traumatize tissue, thereby possibly spreading potentially malignant growth. In addition, use of some types of intravenous injection, such as those which employ intravenous infusion pumps, can be difficult to control and can promote infection. This complication is especially significant for patients afflicted with immunocompromising illnesses (e.g., leukemias and HIV infection).

One attempt to solve problems presented by transfer of molecules and ions across tissues, in particular skin tissue, is employment of a phenomenon called electroporation. Generally, electroporation is a method of temporarily or permanently increasing the permeability of tissue and cell membranes, and simultaneously providing an electrical driving force. The increased permeability allows transport or migration, of chemical agents through the tissue or across cell membranes into cells. Electroporation has been used to deliver drugs to tissue, in vivo, by applying electrodes to the surface of an organism and applying a voltage between the electrodes which exposes the tissue to an electric field. The tissue becomes electroporated and allows delivery of a chemical agent, such as a drug, which has been applied either topically to the organism or injected into the bloodstream of the organism, across the electroporated tissue and into cells of the electroporated tissue.

The effect of electroporation on tissue can be temporary or long-lasting. Without continued application of an electric field, electroporated tissue often reverts back to its original condition. However, the duration of electroporation is dependent upon the degree of electroporation of the tissue. In other words, to obtain a longer duration of electroporation, the period of time of applied voltage, or the amount of voltage applied, must be increased. However, discharge of electrical pulses to skin usually causes sensation by the individual receiving treatment. That sensation is caused by applying an electrical voltage to skin is well known. Often, to create a period of electroporation that is sufficient to deliver a therapeutic amount of a chemical agent, the period of pulsation and/or the required voltage can be uncomfortable or even painful to a patient.

Therefore, a need exists for a new apparatus for electroporating tissue.

SUMMARY OF THE INVENTION

The present invention relates to a new apparatus and method for electroporation of tissue.

The apparatus includes a perforate electrically insulating layer, a first electrode at a first side of the perforate electrically insulating layer and a second electrode at a second side of the perforate electrically insulating layer whereby an electric field extending between the first and second electrodes will preferentially extend through perforations of the electrically insulating layer. The electric field thereby causes electroporation of a tissue that is proximate to the first electrode and is partitioned from the electrically insulating layer and the second electrode by the first electrode.

In one embodiment, the apparatus includes an outer wall and an inner electrically-insulating wall. The inner electrically-insulating wall is recessed within the outer wall. The inner and outer walls define first and second reservoirs. A first electrode is at said first reservoir and a second electrode is at said second reservoir, whereby an electric field extending between electrically-conductive compositions within said first and second reservoirs will extend around the inner electrically-insulating wall and through tissue, at said outer and inner walls, that is in contact with the electrically conductive compositions, the electric field thereby causing electroporation of tissue that is proximate to the electrically conductive compositions.

The method includes applying at least one first electrode to the tissue and forming an electric field between the first electrode and a second electrode that is partitioned from the first electrode by a nonconductive layer. The electric field extends around at least a portion of the insulating layer, whereby the electric field causes electroporation of tissue that is proximate to the first electrode.

The apparatus of the invention has several advantages. For example, an electric field generated between the first and second electrodes will preferentially be limited to perforations of the electrically insulating layer and portions of tissue, such as skin, most proximate to those perforations. Further, electric field lines that extend from one electrode at the tissue to another electrode located away from the tissue will generally limit the depth of the electric field lines within the tissue. This is particularly advantageous for skin tissue, wherein nerve endings lie between about 75 and about 100 micrometers below the surface layer, or stratum corneum, of the skin. Limiting the depth of electric field lines by use of the apparatus of the invention enables electroporation of the stratum corneum without stimulating nerve endings, thereby substantially preventing sensation, including pain, and also preventing stimulation of muscle and associated tissue movement. In other embodiments, the electric field lines can be controlled by, for example, adjusting the amount of applied voltage to the electrodes, to thereby control the amount of sensation during electroporation.

DETAILED DESCRIPTION OF THE INVENTION

Figure 1:
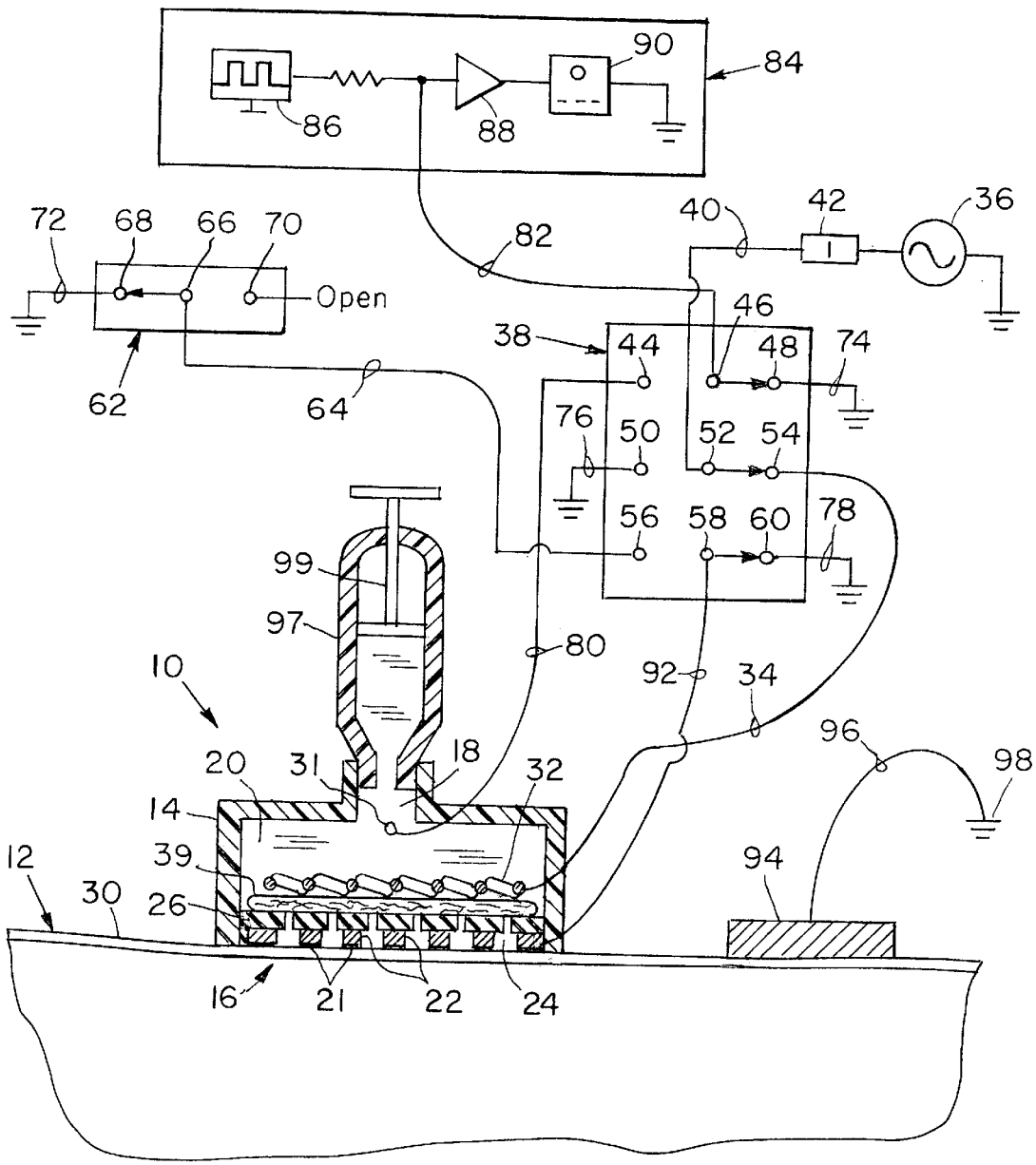
FIG. 1 is a schematic representation, shown partly in cross-section, of one embodiment of the apparatus of the invention.

The features and other details of the apparatus and method of the invention will now be more particularly described and pointed out in the claims. It will be understood that the particular embodiments of the invention are shown by way of illustration and not as limitations of the invention. The principal features of this invention can be employed in various embodiments without departing from the scope of the invention.

Generally, electroporation is a method of increasing the permeability of tissue and cell membranes and simultaneously providing a driving force for molecular transport. The increased permeability allows transport, or migration, of chemical agents through the tissue or across cell membranes into cells. For example, electroporation can include applying a voltage across tissue in vitro to cause the permeability of the tissue and cell membranes of cells in the tissue to increase. If the tissue is in the presence of a suitable chemical agent, the chemical agent can then migrate across the tissue or into cells of the tissue. Electroporation has also been used to deliver drugs to tissue, in vivo, by applying electrodes to the surface of an organism and applying a voltage between the electrodes which exposes the tissue to an electric field. The tissue thereby becomes electroporated and allows delivery of a chemical agent, such as a drug, which has been applied either topically to the organism or injected into the blood stream of the organism, across the electroporated tissue and into cells of the electroporated tissue.

"Electroporation," as that term is used herein, means increased permeability of a cell membrane and/or at least a portion of cells of a targeted tissue to a chemical agent or other suitable material, wherein the increased permeability is caused by application of voltage across the cell or at least a portion of the tissue. An example of a suitable target tissue would be skin tissue, or epidermis, including the multilamellar bilayer membrane within the stratum corneum and also envelopes of keratinocytes. The chemical agent can thereby migrate into or across the electroporated tissue and/or across the cell membrane and into the cell.

Examples of apparatus that have been used for electroporation are disclosed in U.S. Ser. No. 07/705,778, filed May 28, 1991 and in U.S. Pat. No. 5,091,034, issued May 28, 1991, the teachings of which are incorporated by reference in their entirety. Other methods can also be employed, such as those described in U.S. Patent Application entitled, "Introduction of Modifying Agents into Skin by Electroporation," by James C. Weaver, Thomas E. Zewert, Uwe Pliquett, Rita Vanbever, Mark R. Prausnitz, Tani Chen, Christopher Cullander, Richard Guy and Robert S. Langer, Ser. No. 08/695,367, pending, the teachings of which are incorporated herein in their entirety. For example, electric pulses generated by suitable apparatus to cause electroporation by the method of the invention typically are exponential pulses having a time constant in the range of between about 0.1 and about 3 milliseconds, but in some cases as long as about 300 milliseconds, and an amplitude in the range of between about 30 and 1000 volts across the electrodes, which results in smaller voltages across the skin. However, the pulse configuration can also be square, bipolar, etc. Generally, the number of pulses sufficient to cause electroporation is in the range of between about 1 and about 10, wherein the interval between pulses is in the range of between about 0.01 second and 1 minute. Usually the largest increase in permeability caused by electroporation occurs as a consequence of applying the first pulse.

In one embodiment, the apparatus represented in FIG. 1 can be employed. As shown in FIG. 1, electrode/reservoir device 10 is located at epidermis 12 of a human patient. Electrode/reservoir device 10 includes housing 14 that defines application opening 16 and inlet 18. Housing 14 is suitable for containing composition 20, at least one component of which is to be administered to the patient. First electrode 22 is located at application opening 16 within housing 14 and contacts epidermis 12. As shown in FIG. 1, first electrode 22 is a perforate plate. Perforations 24 in first electrode 22 typically have a diameter in a range of between about 5 µm and 500 µm, and, preferably, in a range of between about 10µ and 50 µm. However, first electrode 22 can be alternatively, a bar, a wire mesh, a plate with slit-shaped holes, or have some other configuration. Perforate electrically-insulating layer 26 is located above first electrode 22.

In the case of skin tissue, electrode/reservoir device 10 causes the electric field to be mostly confined to the stratum corneum, i.e., minimal penetration of the electric field into the viable epidermal tissue adjacent the stratum corneum. Accordingly, the diameter of the hole(s) in first electrode 22 is generally chosen to be larger than the diameter of the hole(s) in electrically insulating layer 26. For example, if a 50 µm diameter hole is used in electrically insulating layer 26, the hole diameter is first electrode 22 can be about 80 µm, which provides an annular gap between the two holes of about 15 µm. Generally the width of the annular gap should be approximately equal to the thickness of the stratum corneum. Thus, for human skin with a stratum corneum thickness of about 20 µm, the width of the annular gap should be in a range of between about 1 µm and about 50 µm, and preferably in a range of between about 5 µm and about 30 µm. The thickness of the electrically conducting layer comprising first electrode 22 can also be important. If layer 22 is not recessed into layer 26, then the thickness of layer 22 should be smaller than the thickness of the stratum corneum, i.e., smaller than about 20 µm. Specifically, unless first electrode 22 is recessed into layer 26, the thickness of layer 22 should be in a range of between about 10 nm ($10^{-8}$ m) and about 10 µm, preferably in a range of between about 0.1 µm and about 1 µm. The lower bound for the thickness of first electrode 22 is determined primarily by the objective of having a low electrical resistance and of having a sufficient thickness of electrode material that the electrode is stable with respect to oxidation, electro-erosion and mechanical stress.

Composition 20 is intended to supply or receive transported molecules or ions, and is contained within housing 14 in fluid communication with epidermis 12 through aligned perforations 24 of perforate electrically-insulating layer 26 and first electrode 22. Second electrode 32 is located above perforate electrically-insulating layer 26. Wire 34 connects second electrode 32 to voltage source 36 at switch 38. An example of a suitable voltage source 36 is an exponential voltage pulse generator. In another embodiment, an electric current or charge source can be used instead of a voltage source.

Switch 38 includes terminals 44, 46, 48, 50, 52, 54, 56, 58 and 60. Ground connections 74, 76, and 78 extend from terminals 48, 50, and 60, respectively.

Wire 80 extends from resistance-measurement electrode 31 to terminal 44 of switch 38. Wire 82 extends from terminal 46 of switch 38 to resistance measurement device 84, which includes signal generator 86, amplifier 88, oscilloscope 90 and an electrical ground. Wire 92 extending from first electrode 22 extends to terminal 58 of switch 38.

Electrode 94 is located at epidermis 12 of the patient. Optionally, electrode 94 can be omitted from electrode/reservoir 10. Wire 96 extending from electrode 94 is connected to ground 98. Typically, electrode 94 is located between about five and about twenty centimeters from housing 14.

Filter 39 is located between perforate electrically-insulating layer 26 and second electrode 32. Optionally, filter 39 can be omitted from electrode/reservoir device 10. Filter 39 can be formed of a suitable electrically nonconducting material, such as cellulose, polyimide, etc. In another embodiment of the present invention, filter 39 can be a membrane formed of suitable electrically nonconducting material, such as suitable filters having a pore size in a range of between about 0.2 and about 100 micrometers.

In another embodiment, voids created by perforate electrically-insulating layer 26, aligned perforations 24 of perforate electrically-insulating layer 26, first electrode 22, filter 39, or combinations thereof, can be filled with composition 20, thereby eliminating the need for excess composition 20 in housing 14. Composition 20 should be in fluid communication with epidermis 12.

Optionally, housing 14 can be omitted. This can be accomplished by placing second electrode 32 above perforate electrically-insulating layer 26. Voids created by electrically-insulating layer 20, aligned perforations 24 of perforate electrically-insulating layer 26, first electrode 22, and, optionally, filter 39 are filled with composition 20, thereby providing fluid communication of composition 20 between electrode 22 and epidermis 12.

The electrodes of electrode/reservoir device 10 are typically composed of a suitable conductive material, such as copper, gold, aluminum etc., but can also include semiconductors, such as silicon, germanium, or resistive conductors, such as carbon. Perforate electrically-insulated layer 26 is formed of a suitable electrically nonconducting material, such as a suitable polyimide, Mylar, etc. Housing 14 is typically composed of a suitable material, such as plastics and other non-electrically conductive materials. Generally, the diameter of perforations 24 at electrode 22 are larger than the diameter of perforations 24 at electrically-insulating layer 26, thereby providing an annular gap at the interface between first electrode 22 and electrically-insulating layer 26.

Figure 2:
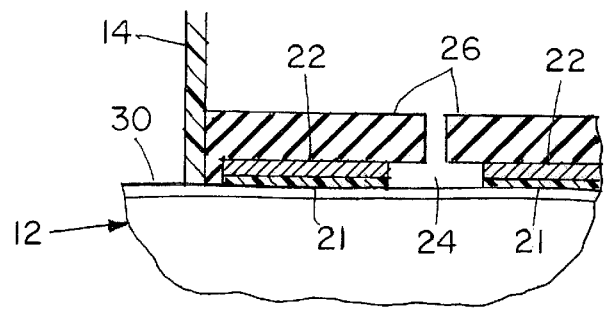
FIG. 2 is a cross-section view of a portion of the apparatus shown in FIG. 1.

In one embodiment, as can be seen in FIG. 2, at least a portion of the surface of perforate electrode 22 is provided with a coating of electrically insulating dielectric material 21, thereby providing an electrical capacitance. This capacitance serves the purpose of diminishing or preventing electrolysis at the aqueous solution/electrode interface and thereby reduces gas evolution and bubble formation within the electrode/reservoir device. Such bubbles are generally undesirable, as their presence interferes with the flow of electrical currents along the intended pathways. Suitable materials for an electrically insulating dielectric coating 21 include Teflon®, Mylar®, etc. and oxides such as aluminum oxide and tantalum oxide.

Composition 20 within housing 14 is electrically conductive. Composition 20 typically includes a material that can be transported, by migration or some other mechanism, across epidermis that has been electroporated. In one embodiment, composition 20 is a solution, wherein the agent and/or material are solutes of the solution. Examples of suitable solvents include physiological saline, phosphate buffered saline or other aqueous electrolytes of known pH, distilled water with known trace electrolytes, etc. An electrically conductive gel or paste containing a material to be introduced into epidermis 12 can be employed as composition 20.

Returning to FIG. 1, the method of the invention includes applying at least one electrical pulse to epidermis 12 by applying a voltage between second electrode 32 and first electrode 22. A localized electric field is formed between second electrode 32 and first electrode 22 that extends within epidermis 12. The amplitude, number, and duration of pulses is sufficient to electroporate epidermis 12 proximate to first electrode 22. Typically, the epidermis is electroporated by applying a voltage from voltage source 36 to second electrode 32 in a range of between about 50 volts and about 500 volts, preferably between about 70 volts and about 200 volts. In one embodiment, the voltage is applied as a series of pulses. In a specific embodiment, the pulse-applied voltage has an average duration in a range of between about 1 milliseconds and about 3 milliseconds per pulse, and the number of pulses employed to cause electroporation of epidermis 12 is in a range of between about 1 and about 10 pulses.

There are two general modes of use for the electrode/reservoir device 10, an electrical pulsing mode or a resistance measurement mode, with the pulse/measurement choice implemented by using switch 38. As shown in FIG. 1, switch 38 is set in the "pulsing mode," such that a voltage pulse produced by pulse generator 36 results in electrical current flow through wire 40, which passes through current sampling resistor 42 and flows to terminal 52 of switch 38, and then (in the position shown) reaches terminal 54 of switch 38, which is connected by wire 34 to conduct the current into electrode/reservoir device 10 to reach second electrode 32, and then passes through electrically conducting fluid (composition) 20, through filter 39, through one or more holes in electrically insulating layer 26, and then into and through epidermis 12, where the current spreads out and reaches perforate electrode 22, with the current exiting electrode/reservoir device 22 along wire 92 to reach terminal 58 of switch 38, and then to terminal 60 of switch 38, which is connected to ground that provides a return path to pulse generator 36. During such pulsing the skin resistance measurement system 84 is connected by wire 82 to terminal 46 of switch 38, and then in the switch position shown, connected to terminal 48, which is connected to ground 74, with this grounding of measurement system 84 serving to protect said measurement system from stray currents and capacitive pickup during pulsing.

During measurements carried out before or after pulsing, two different measurement modes can be used, one without the use of separate electrode 94, and one which involves electrode 94. For the switch position shown for measurement mode selection switch 62 separate electrode 94 is not involved. In this mode, a small resistance measurement current, for example a small amplitude square wave current (as indicated in resistance measurement device 84), flows from square wave generator 86 within resistance-measurement device 84 through wire 82 to terminal 46 of switch 38, then to terminal 44 of switch 38 through wire 80 into electrode/reservoir device 10 to resistance-measurement electrode 31, through electrically conducting fluid (composition) 20, through one or more holes in electrically insulating layer 26, and then into and through epidermis 12, where the current spreads out and reaches perforate electrode 22, then through wire 92 to terminal 58 of switch 38, which is now connected to terminal 56 of switch 38, then through wire 64 to terminal 66 of measurement mode selection switch 62, which in the position shown is connected to terminal 68 of switch 62, and then through wire 72 to ground, thereby completing the measurement circuit to the ground of resistance-measurement device 84. Amplifier 88 and oscilloscope 90 can be used to measure the voltage developed because of the square wave current, which provides a measure of the skin or tissue resistance adjacent perforation electrode 22. Note that, in this resistance-measurement mode, separate electrode 94 is usually not present.

In the alternative resistance-measurement mode, resistance-measurement selection switch 62 is put into a second position (not shown). With this setting, the resistance-measurement device measurement current cannot flow out of electrode/reservoir device 10 along wire 92 and into switch 62 to reach ground, because switch 62 is connected to terminal 70, which is electrically open (a very high resistance). Thus, resistance-measurement device measurement current instead flows across the epidermis at the site of one or more holes in perforate electrode 22, but in this case more deeply into the epidermal tissue but with significant current spreading, with the current within the epidermal tissue reaching electrode 94 (electrode area 94 is generally much larger than the total area of the holes in perforate electrode 22), and then through wire 96 to ground 98. In this alternative resistance-measurement mode the resistance-measurement current flows through and within the epidermis at two distinct sites: at the electrode/reservoir device 10 and at the separate electrode 94, but only the resistance of the epidermis adjacent electrode/reservoir device 10 is usually altered by pulsing, and this means that the resistance measurement involving the two sites can be used to infer the resistance changes at the site of the electrode/reservoir device 10.

Although the method of the invention is not to be bound by any particular theory, it is believed that the electroporated portion of epidermis 12 includes stratum corneum layer 30 of epidermis 12. It is also believed that electroporation of epidermis 12 includes temporary disruption of lipid-containing barriers of epidermis 12, thereby causing the formation of aqueous pathways through the lipid-containing barriers, such as multi-lamellar lipid regions of stratum corneum 30 of epidermis 12. The degree or amount of electroporation can be measured following application of electrical pulses by conducting a measurement of electrical resistance across epidermis 12. The measurement of electrical resistance can be obtained by activating electrical resistance measurement device 84. Typically, the degree or amount of electroporation can be indirectly determined as being inversely proportional to the electrical resistance of epidermis 12, adjacent the perforations of electrode/reservoir device 10.

It is also believed that an electric field generated between the first and second electrodes will preferentially be limited to regions at or immediately adjacent to the perforations of the electrically-insulating layer 26 and portions of tissue, such as skin, most proximate to those perforations. Further, electric field lines that extend from one electrode at the tissue to another electrode located away from the tissue will generally limit the depth of the electric field lines within the tissue. Limiting the depth of electric field lines by use of the apparatus of the invention enables electroporation of the surface layer, or stratum corneum, of the skin without stimulating nerve endings, thereby substantially preventing sensation, including pain, and also substantially preventing stimulation of muscles, thereby also substantially preventing associated tissue movement. In other embodiments, the electric field lines can be controlled by, for example, adjusting the amount of applied voltage to the electrodes, to thereby control the amount of sensation.

Electroporation of epidermis 12 causes composition 20 to migrate from within housing 14 and into or across epidermis 12. The material is transported into or across the electroporated epidermis by a mechanism, such as active transport or diffusion, at a rate that is greater than that which would occur into or through epidermis that has not been electroporated. Optionally, the rate of transport of the material into or through epidermis 12 can be further facilitated by application of other suitable forces. Examples of suitable forces are a mechanical force, such as hydrostatic pressure, osmotic pressure, and electrocompression or ultrasound. Separate or independent stimulation of muscle to cause tissue movement can also be used to provide pressure for this purpose. In one specific embodiment a mechanical force can be applied by pressurizing composition 20 that includes the material within housing. Composition 20 can be pressurized by a suitable method, such as by applying pressure to syringe 97 at inlet 18 of housing 14. Alternatively, fluids can be withdrawn from a patient through an electroporated tissue region into housing 14 by withdrawing plunger 99 of syringe 97, i.e. by applying negative pressure (suction), or by applying an electrical driving force in the outward direction, e.g., by pulses of suitable polarity.

In another embodiment, transport of the material into or across electroporated epidermis can be facilitated by additional application of an electric field across the electroporated epidermis, whereby the rate of iontophoretic transport of the material across the epidermis 12 is increased.

Figure 4:
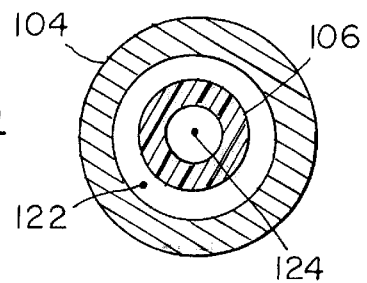
FIG. 4 is a plan view of the concentric tube embodiment of the invention shown in FIG. 3, taken along line IV—IV.
Figure 3:
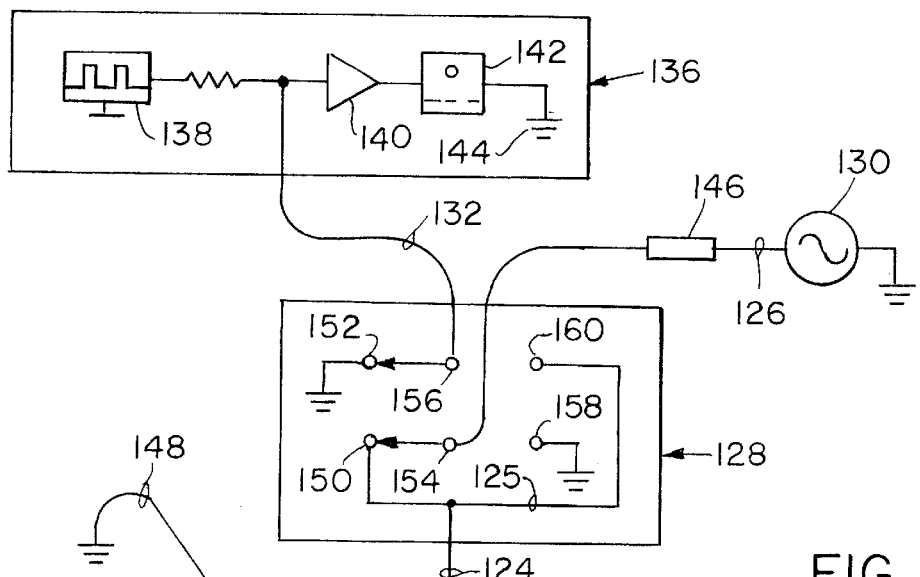
FIG. 3 is a side view, shown in cross-section, of a concentric tube embodiment of the invention.
Figure 3:
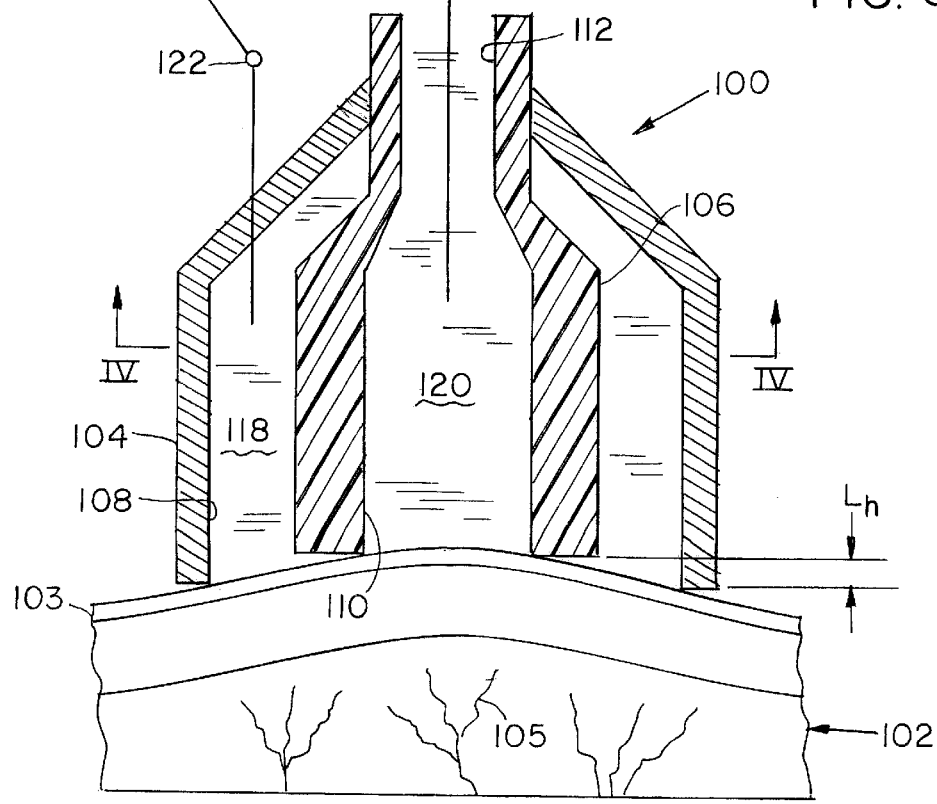

In another embodiment, the apparatus represented in FIGS. 3 and 4 can be employed. As shown in FIG. 3, tube/reservoir device 100 is located at epidermis 102 of a human patient. Tube/reservoir device 100 includes outer wall 104 and inner electrically-insulating tube wall 106. The alignment of the inner and outer tubes does not need to be concentric. Outer wall 104 defines application opening 108. Inner electrically-insulating tube wall 106 defines application opening 110 and opening 112. A syringe can be fitted to opening 112. Application opening 110 is recessed within outer wall 104. Optionally, application opening 110 does not need to be recessed. Outer wall 104 and inner electrically-insulating tube wall 106 define a first reservoir containing first electrically-conductive composition 118. As shown in FIG. 4, outer wall 104 and inner electrically-insulating tube wall 106 are concentric, but a centric alignment is unnecessary.

Referring back to FIG. 3, inner electrically-insulating tube wall 106 defines a second reservoir containing second electrically-conductive composition 120. First electrically conductive composition 118 is in fluid communication with epidermis 102 at stratum corneum layer 103 and is contained by the first reservoir and by epidermis 102. Second electrically-conductive composition 120 is in fluid communication with epidermis 102 at stratum corneum layer 103 by the second reservoir and epidermis 102. First electrically-conductive composition 118 is partitioned from second electrically-conductive composition 120 by inner electrically-insulating tube wall 106 and by epidermis 102. First electrode 122 is located at the first reservoir and is in communication with first electrically conductive composition 118. Second electrode 124 is located at the second reservoir and is in communication with second electrically-conductive composition 120. Wire 125 extends from switch 128 to second electrode 124. Wire 126 connects terminal 154 of switch 128 through current sampling resistor 146 to voltage source 130. An example of a suitable voltage source 130 is an exponential voltage pulse generator. An electric current or charge source can also be used instead of a voltage source.

Wire 132 extends from switch 128 to electrical resistance measurement device 136. Electrical resistance measurement device 136 includes signal generator 138, amplifier 140, oscilloscope 142 and electrical ground 144. Electrode 124 can be employed to measure electrical resistance at epidermis 102 by turning switch 128 from connection with voltage source 130 to connection with electrical resistance measurement device 136. A separate electrode 94 (see FIG. 1) can also be used to make an electrical resistance measurement, but in this case the resistance of the skin at a second site, that of electrode 94, is in series with the skin subject to electroporation. Generally the skin resistance at the site of electrode 94 changes insignificantly during pulsing, and therefore this arrangement can also be used to assess skin resistance changes associated with skin electroporation.

Epidermis 102 extends within outer wall 104 to contact inner electrically-insulating tube wall 106. The difference in position between application opening 108 and application opening 110 is measured as $L_h$. The dimension $L_h$ generally is in a range of between about zero and about one-quarter of the internal diameter of outer tube wall 104. The thickness of inner electrically-insulating wall 106 should generally be about the thickness of stratum corneum layer 103. Also the width of the annular gap between inner wall 108 of outer tube 104 and inner electrically-insulating tube 106 should generally be about the same as the thickness of stratum corneum layer 103, which is typically between about 15 $\mu$m and 20 $\mu$m in thickness.

First electrode 122 and second electrode 124 of tube/reservoir device 100 are typically composed of a suitable conductive material, such as copper, gold, aluminum etc. Inner electrically-insulated tube 106 is typically formed of a suitable electrically nonconducting material, such as a plastic or other electrically nonconductive material. Outer tube 104 is also typically formed of an electrically nonconductive material, but can also be constructed of a conductive material, such as stainless steel.

Electrically conductive compositions 118, 120 include materials that can be transported, by migration or some other mechanism, across a portion of epidermis that has been electroporated. In one embodiment, either electrically conductive composition 118 or 120 can be a solution, wherein the agent and/or material are solutes of the solution. Examples of suitable solvents include physiological saline, phosphate buffered saline, distilled water with known trace electrolytes, etc. An electrically conductive gel or paste containing a material to be introduced into or through stratum corneum 103 by the method of the invention can also be employed as electrically conductive composition 118 and/or 120. Examples of suitable materials for electrodes 122 and 124 include electrically conductive materials such as aluminum, etc., and also semiconducting materials such as silicon and germanium, and resistive materials such as carbon.

The method of the invention includes applying at least one electrical pulse to epidermis 102 by applying a voltage between second electrode 124 and first electrode 122. Alternatively, a current or charge pulse can be applied. A localized electric field is thereby formed between first composition 118 and second composition 120 that extends around inner electrically-insulating tube wall 106 at application opening 110 and within epidermis 102. The amplitude, number, and duration of pulses is sufficient to electroporate epidermis 102 proximate to first composition 118 and second composition 120. Typically, the epidermis is electroporated by applying a voltage from voltage source 130 in a range of between about 30 volts and about 1000 volts, and preferably between about 70 volts and about 200 volts. In one embodiment, the voltage is applied as a series of pulses. In a specific embodiment, the pulse-applied voltage has an average duration in a range of between about 1 milliseconds and about 3 milliseconds per pulse, but can be as long as 300 milliseconds, and the number of pulses employed to cause electroporation of epidermis 102 is in a range of between about 1 and about 10 pulses.

There are two general modes of use for the electrode/reservoir device 100, an electrical pulsing mode or a resistance measurement mode, with the pulse/measurement choice implemented by using switch 128. As shown in the drawing, switch 128 is set in "pulsing mode," with terminals 150 and 154 connected to each other and terminals 152 and 156 connected to each other. In this mode, a voltage pulse produced by pulse generator 130 results in electrical current flow through wire 126 which passes through current sampling resistor 146 and flows to terminal 154 of switch 128, then to terminal 150 of switch 128, which is connected to electrode 124, and then passes through electrically conducting fluid (composition) 120, through stratum corneum 103 and epidermis 102, where the current spreads out and reaches electrically conducting fluid (composition) 118, and then to electrode 122 to ground 148. This completes the pulsing circuit.

During such pulsing, the skin resistance measurement system 136 is connected by wire 132 to terminal 156 of switch 128, and then (in the switch position shown) to terminal 152, which is connected to ground. This grounding of resistance measurement system 136 serves to protect said system from stray currents and capacitive pickup during pulsing.

During measurements carried out before or after pulsing, switch 128 is placed in the other position, so that terminals 154 and 158 are connected to each other, and terminals 156 and 160 are connected to each other. In this mode, a small resistance measurement current, for example a small-amplitude square wave current (as indicated in signal generator 138) flows from resistance measurement system 136 through wire 132 to terminal 156 of switch 128, then to terminal 160 of switch 128, which is connected to electrode 124, and then passes through electrically conducting fluid (composition) 120, through stratum corneum 103 and epidermis 102, where the current spreads out and reaches electrically conducting fluid (composition) 118, and then to electrode 122 to ground 148. This completes the resistance measurement circuit.

During such resistance measurement, the pulse generator 130 is connected by wire 126 through current sampling resistor 146 to terminal 154 of switch 128, and then (in the switch position not shown) to terminal 158, which is connected to ground. This grounding of pulse generator 130 serves to protect the resistance measurement system 136 from stray currents and capacitive pickup during measurement.

It is believed that an electric field generated between first electrically-conductive composition 118 and second electrically-conductive composition 120 will preferentially be limited to penetration of epidermis 102 most proximate to the first and second electrically-conductive compositions. Further, electric field lines that extend from one electrically-conductive composition to another electrically-conductive composition, separated by a distance defined by the thickness, typically about 20 micrometers to about 100 micrometers, of electrically-insulating tube 106, and the parameter $L_h$ generally limits the depth of the electric field lines within the tissue. Typically, $L_h$ ranges from a value of about zero to about one quarter of the internal diameter of outer wall 104. Controlling the voltage enables control of the depth of electric field lines by use of the apparatus of the invention. Thus, the surface layer, or stratum corneum, of epidermis 102 can be electroporated in a controlled manner without stimulating nerve endings 105, thereby enabling control of sensation, or substantially preventing pain, and also substantially preventing stimulation of muscles, thereby substantially preventing associated tissue movement.

Figure 6:
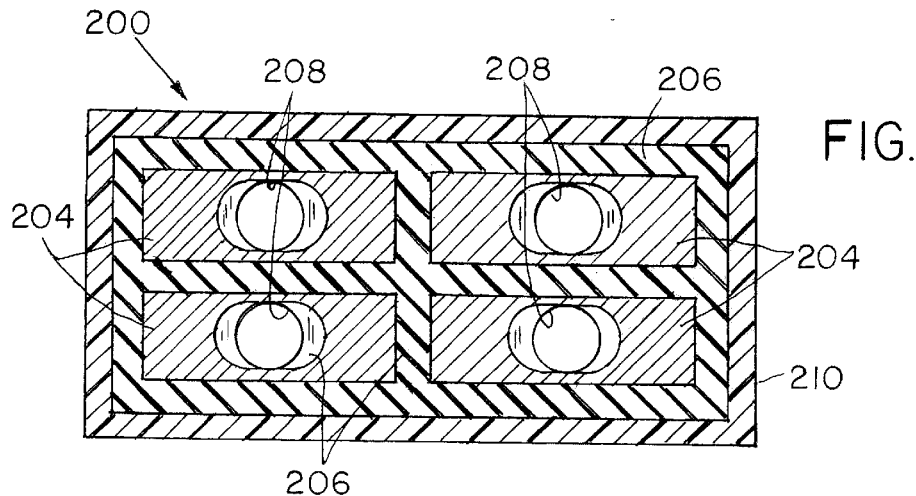
FIG. 6 is a plan view of the embodiment of the invention shown in FIG. 5, taken along lines VI—VI.
Figure 5:
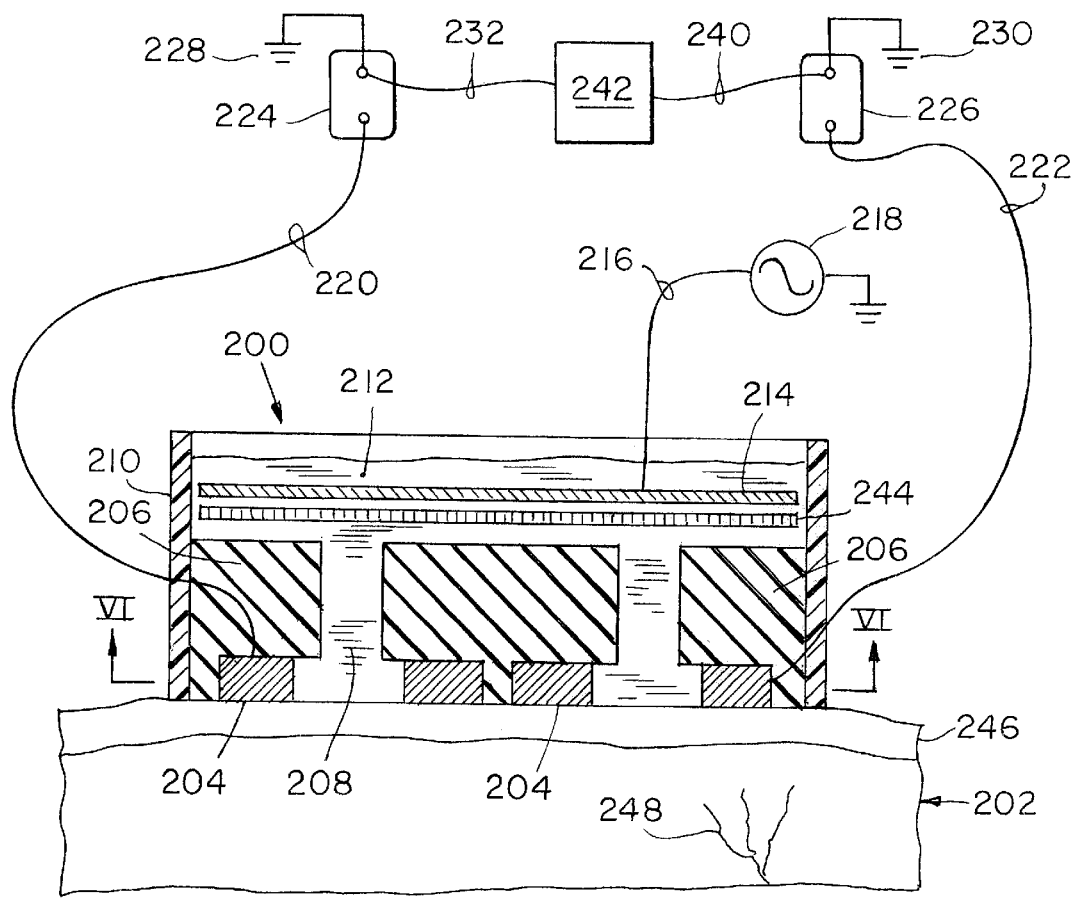
FIG. 5 is a side view, shown in cross-section, of an embodiment of the invention having a plurality of first electrodes separated by an electrically insulating layer.

In still another embodiment, the apparatus represented in FIGS. 5 and 6 can be employed, which allows the site(s) of electroporation to be electrically addressed. As shown in FIG. 5, device 200 is located at epidermis 202 of a human patient. Device 200 includes a plurality of first electrodes 204 that contact epidermis 202. Perforate electrically-insulating layer 206 is located at first electrodes 204. Perforate electrically insulating layer 206 also separates multiple first electrodes 204. Conduits 208 are defined by first electrodes 204 and by perforate electrically-insulating layer 206. Housing 210 extends about electrically-insulating layer 206. Composition 212 is contained within housing 210 and is in fluid communication with epidermis through conduits 208. Second electrode 214 is located above perforate electrically-insulating layer 206 and is immersed in composition 212. Wire 216 extends from second electrode 214 to voltage source 218. An example of a suitable voltage source 218 is an exponential voltage pulse generator.

Wires 220, 222 extend from separate first electrodes 204 to switches 224, 226, respectively. Ground wires 228, 230 extend from switches 224, 226, respectively. Wires 232, 240 extend from switches 224, 226, respectively, to microprocessor 242. Switches 224, 226 are separately controllable by microprocessor 242. It is to be understood that additional switches, having the same configuration, are located between microprocessor 242 and other first electrodes of the array shown in FIG. 6. As shown in FIG. 6, first electrodes 204 can be arranged as of an array, whereby electric fields can be formed at individual first electrodes 204, or patterns thereof, to determine a preferred location or locations for electroporation of epidermis 202. Microprocessor 242 controls which of first electrodes 204 can be used to stimulate electroporation. Microprocessor 242 can be employed to control formation of electric fields at individual first electrodes 204 and to determine preferred lateral locations of epidermis for electroporation.

Referring back to FIG. 5, filter or microporous gel layer 244 is located between perforate electrically insulating layer 206 and second electrode 214. Optionally, filter 244 can be omitted from device 200. Filter 244 can be formed of a suitable electrically nonconducting material, such as cellulose, polyimide, etc. Examples of suitable microporous gel materials include agarose, polyacrylamide, etc. In another embodiment of the present invention, filter 244 can be a membrane formed of suitable electrically nonconducting material, such as a filter having a pore size in a range of between about 0.2 and about 100 micrometers.

The electrodes of device 200 are typically composed of a suitable conductive material, such as copper, gold, aluminum, etc., or semiconductors, such as silicon, germanium, or resistive materials, such as carbon. Perforate electrically-insulating layer 206 is formed of a suitable electrically nonconducting material, such as a suitable polyimide, etc.

Composition 212 within perforate pore or conduit 208 is electrically conductive. Composition 212 typically includes a material that can be transported, by migration or some other mechanism, across a portion of epidermis 202 that has been electroporated. In one embodiment, composition 212 is a solution, wherein the agent and/or material are solutes of the solution. Examples of suitable solvents include physiological saline, phosphate buffered saline, distilled water with known trace electrolytes, etc. An electrically conductive gel or paste containing a material to be introduced into or through stratum corneum 246 by the method of the invention can also be employed as electrically conductive composition 212.

At least one electrical pulse is applied to epidermis 202 at stratum corneum layer 246 by applying a voltage between second electrode 214 and first electrode 204. Alternatively, a charge pulse or current pulse can be used. A localized electric field is formed between second electrode 214 and first electrode 204 that extends within epidermis 202. The amplitude, number, and duration of pulses is sufficient to electroporate epidermis 202 proximate to first electrode 204. Typically, the epidermis is electroporated by applying a voltage from voltage source 218 in a range of between about 50 volts and about 200 volts. In one embodiment, the voltage is applied as a series of pulses. In a specific embodiment, the pulse-applied voltage has an average duration in a range of between about 1 milliseconds and about 3 milliseconds per pulse, and the number of pulses employed to cause electroporation of epidermis 202 is in a range of between about 1 and about 10 pulses. Microprocessor 242 can be utilized to generate trial voltage pulses. The trial voltage pulses can be used to identify any one or more lateral regions of epidermis 202 with reduced sensitivity. For example, first electrodes can be selectively activated to identify first electrodes most distant from nerve ending 248 of epidermis 202. Once identified, first electrodes 204 that are most distant from nerve endings 248 can then be selectively employed to electroporate epidermis and to deliver composition 212 into epidermis 202 without causing discomfort to, or undesired muscle movement in, the patient. Subsequent pulsing of the affected area allows electroporation without causing discomfort to, or undesired muscle movement in, the patient.

Although it is generally preferred to use the apparatus of this invention with pulses in a range of between about 50 volts and about 500 volts, because such pulses cause electroporation within the stratum corneum, and result in the largest molecular transport, the apparatus can also be used with pulses in a range of between about 5 volts and about 50 volts, because pulses in this range predominantly cause electroporation of the linings of sweat gland ducts.

The apparatus of this invention can also be used to transport molecules across tissue without necessarily causing electroporation. Unlike electroporation of the stratum corneum, which is caused by large pulses (between about 50 volts and about 500 volts at the electrodes) iontophoresis is often caused by application of essentially steady (direct current) relatively small voltages (between about 0.1 volt and about 5 volt) or currents, which transport molecules through pre-existing pathways. In the case of transdermal molecular transport for drug delivery or chemical analyte extraction, the apparatus can be used with iontophoresis by using much smaller voltages, typically in the range of 0.1 volt to 5 volt (see, for example, B. H. Sage, "Iontophoresis" in Percutaneous Penetration Enhancers E. W. Smith and H. I. Maibach, Eds., CRC Press, pp. 351–368, 1995, and references contained therein, and also J. A. Tamada, N. J. V. Bomannon and R. O. Potts "Measurement of Glucose in Diabetic Subjects Using Noninvasive Transdermal Extraction" Nature Medicine 1:1198–1202, 1995). When used with iontophoresis, the skin resistance changes much more slowly, and much less in magnitude, and this skin resistance behavior is believed to be due to changes of ionic composition of solutions with pre-existing aqueous pathways (see, for example, S. M. Dinh, C-W. Luo and B. Berner "Upper and Lower Limits of Human Skin Electrical Resistance in Iontophoresis" AIChe J. 39:2011–2018, 1993). Thus, the larger skin resistance during iontophoresis means that the electric field is more confined to the stratum corneum than for electroporated skin if iontophoresis is used with the apparatus of this invention, and electrode/reservoir device dimensions should be chosen accordingly. Generally, however, because of the larger skin resistance during iontophoresis, electrode/reservoir devices designed for the use with electroporation serve to also suitably confine the electric field at the lower voltages used with iontophoresis, because of the larger skin resistance associated with iontophoresis. The apparatus of this invention allows transdermal iontophoresis but avoids deeply penetrating electric fields and their associated currents, and this minimizes electrical interactions with the viable epidermis which can cause irritation and other undesired side effects." An additional feature of the apparatus of this invention is that no electric field or currents cross the stratum corneum at sites other than the site of the device, unless a separate electrode 94 is used for combined measurement of the skin resistance at two sites.

The invention will now be further and specifically described by the following examples. All parts and percentages are by weight unless otherwise specified.

Exemplification

EXAMPLE 1

The apparatus and process of the invention were partially illustrated by designing, constructing, and using a hand-drilled electrode array version of an electrode/reservoir device with seven (7) holes (350 $\mu$m diameter, 300–600 $\mu$m apart, with the perforate electrode formed from a 25 $\mu$m thick copper layer attached to a 50 $\mu$m thick polyimide electrically insulating layer). Several experiments in vitro tested the suitability of the device for transdermal molecular transport. The results demonstrate that charged molecules were transported locally across the skin at the sites of the holes by using gel trapping microscopy (see Pliquett, U. F. et al., "Imaging of Fluorescent Molecule and Small Ion Transport Through Human Stratum Corneum During High-Voltage Pulsing: Localized Transport Regions are Involved," J. Biophys. Chem. 58, 185–204, [1996]).

This experiment involved applying the prototype electrode/reservoir device (a version of FIG. 1) against the stratum corneum side of a human skin preparation mounted on gelled agarose, with the agarose layer serving to inhibit convection. The donor compartment contained PBS+1 mM calcein and the counter (second) electrode. The electrode/reservoir device was pressed to the skin's surface (with about 100 Pa pressure), and a series of $N_{pulse}$=200 exponential pulses ($\tau_{pulse}$≈1 ms; maximum transdermal voltage $U_{skin,0}$≈150 volts (V)) was delivered. The skin was examined by fluorescence microscopy, and calcein (green fluorescence) observed. We observed green fluorescent rings with the same diameter as the holes of the electrode. The center region was considerably dimmer than the edge, probably resulting from the high resistance of the saline compared to the metal electrode. This means that there was not an equipotential across the 350 $\mu$m diameter hole, but instead higher fields near the hole edge. Calcein was also found in the gel, but it had diffused laterally within the gel to form a bright region underneath the skin. It nevertheless confirms that transport across the skin took place. Our interpretation is that calcein was successfully transported locally across human skin, as desired.

EXAMPLE 2

A very similar electrode/reservoir device was used to demonstrate that very little sensation was perceived in vivo. Specifically, the ability of the prototype device to minimize and/or avoid sensation and pain was tested by two human volunteers (Drs. U. Pliquett and J. C. Weaver). Both human volunteers self-administered a series of progressively larger pulses while holding the prototype array against their forearm. This prototype had 48 holes, each 350 $\mu$m in diameter, and was constructed from gold-covered Kapton® polyimide. Two sites were used: (1) dry skin, and (2) skin hydrated by saline contact for ½ hour. Dry skin has much larger $R_{skin}$, and resulted in less sensation; therefore the more relevant (to transdermal drug delivery) hydrated skin result is briefly described.

The array reservoirs (300 $\mu$m diameter holes) were filled with saline, to make contact with the skin. Single exponential pulses ($\tau_{pulse}$=1 ms) were self-administered, starting at 10 V. For one subject, (JCW), at approximately 150 V a clear perception (a "faint pricking") occurred, and as the voltage was decreased, the perception now occurred at smaller voltages. However, throughout, there was no major pain. A few different sites were tried, by moving the entire array (there was no site addressing capability in the prototype). Only slight differences were then experienced. For the second subject, (UP), a voltage of up to 250 V was applied without sensation. Increasing the voltage resulted in a sensation compared to the touching of the hairs at the skin surface and later to a very short prick sensation. Sometimes also something within the vicinity of the electrode was felt.

Ordinarily, the application of "high-voltage" pulses to skin electrodes is intended to stimulate nerves. (Reilly, J. P. (Ed.) "Electrical Stimulation and Electropathology," Cambridge University Press, Cambridge, 1992). It is probably not surprising, therefore, that even a non-optimal "field-confining" electrode/reservoir device with similar HV pulses failed to cause significant nerve stimulation.

EXAMPLE 3

The invention was further illustrated by another version of the basic apparatus of FIG. 1 in which the hole diameter was much smaller, viz. 20±5 $\mu$m. These were specified by us for fabrication by a commercial source of laser drilling (Laser Services, Inc., Westford, Mass.), using 25 $\mu$m thick polyimide pieces with a bonded copper layer of 25 $\mu$m thickness on one side. The holes were laser drilled starting from the side of the polyimide without copper, to minimize copper deposition onto the hole walls. A center-to-center hole spacing of 300 $\mu$m was used, with a total of about 1,000 holes. This copper-based electrode system changed with pulsing due to electroerosion, and eventually became unrealistic to use.

In the first experiments with this electrode/reservoir device, a series of single exponential pulses ($\tau_{pulse} \approx 1$ ms) was used with the sterile, saline-filled electrode/reservoir device held firmly against a hydrated site on the forearm of a human subject. An ECG electrode (D102 Ag/AgCl, In Vivo Metric, Healdsburg, Calif.) had been placed about 5 cm away, with electrical connections that allowed either "high-voltage" pulsing or resistance measurements. The resistance was that of a series pathway which crossed the skin at two sites: (1) within the electrode/reservoir device, and (2) the ECG electrodes.

In vivo experiments together with manually recorded resistance measurements were performed initially. For the first subject (JCW), the first sensation ("a faint prick") was felt when the applied voltage (between the electrodes) was 300 V, and at the same time the resistance dropped by about 20%. In another experiment, on a second subject (UP), a sensation was not felt until a voltage of 400 V was applied.

Another in vivo experiment with subject UP involved application of single pulses, starting with an electrode voltage across the electrode/reservoir device of 50 V. Thereafter the electrode pulse voltage was increased in 50 V increments, with both the resistance (in series across the skin at both the electrode/reservoir device site and the ECG site) measured and the subjects' perception of sensation noted. After 250 V, the next pulse voltage was chosen to be 270 V (not 275 V), and a measurable decrease of $R_{skin}$ was observed, but there was no sensation. A further pulse of 300 V also caused no sensation, and still other pulses were applied without any sensation.

The same electrode/reservoir device was then used with subject JCW. The value of the two-skin-site resistance before pulsing was $7.2 \times 10^4 \Omega$, but application of a single 150 V pulse across the electrodes resulted in a sudden drop to $5.2 \times 10^4 \Omega$, without any sensation. The next pulse (170 V) caused a further decrease in resistance to $4.8 \times 10^4 \Omega$, which was accompanied by a slight sensation ("a small prick").

A next experiment with subject UP was unsuccessful in the sense that the resistance was always $2.2 \times 10^4 \Omega$, with the lack of response believed to be due to electrodeposition of electrically shunting material across some of the holes. Material in the holes was observed subsequently by microscopy. However, the earlier experiments support the occurrence of localized electroporation without sensation.

EXAMPLE 4

The electrode array of the electrode/reservoir device (FIG. 1) was made from Kapton® polyimide covered with 15 $\mu$m of aluminum at one side, which contacted the skin. The array consisted of 50 $\mu$m diameter holes, with two different spacings present within the array: 50 $\mu$m edge-to-edge and 100 $\mu$m edge-to-edge. (This array had been produced from a test pattern for an entirely different application.) The array was mounted on one side of a filter housing (in place of the filter) and the other side of the housing was removed. A counterelectrode (0.2 mm copper wire) was placed between the supporting plastic in the housing. The electrode was mounted on a 10 cc syringe and filled with saline. For resistance measurements, a second electrode (jD102 Ag/AgCl, In Vivo Metric, Healdsburg, Calif.) was placed within the saline and a second one at the skin surface in the immediate vicinity of the electrode/reservoir device. Note that this resistance is the series resistance across two skin sites, with only one altered by localized skin electroporation (FIG. 1).

A "high-voltage" pulse (with $\tau_{pulse} \approx 0.8$ ms) was delivered by a custom-built pulser through the electrode/reservoir device. The pulse was applied through a high-voltage switch, automatically disconnecting the impedance measurement system for the duration of the pulse.

Figure 7:
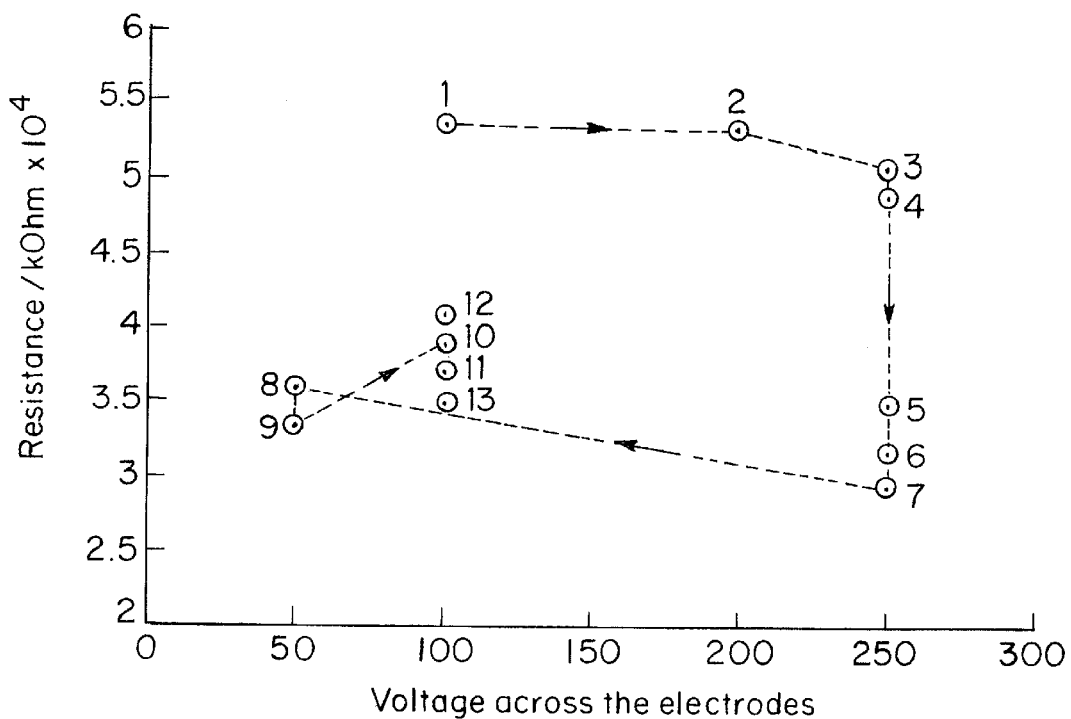
FIG. 7 is a plot of electrical resistance of epidermis of one subject versus pulse voltage applied to the epidermis by the method of the invention.

The voltage (across the electrodes) of the first pulse was 100 V, and was increased until a sensation was felt. A plot of the resistance vs. electrode voltage for a first subject is shown in FIG. 7, in which the sequence of pulses is labeled numerically as points 1 through 13. Then the voltage was not further increased, but the dynamic resistance behavior investigated at the same or lower voltage (in this case 250 V). In this subject, a hint of sensation occurred at points 3 and 4, with stronger sensation at points 5, 6, and 7. Sensation was no longer felt at Point 8 and beyond. The dynamic changes in resistance were still observed, and are interpreted as evidence for electroporation.

Figure 8:
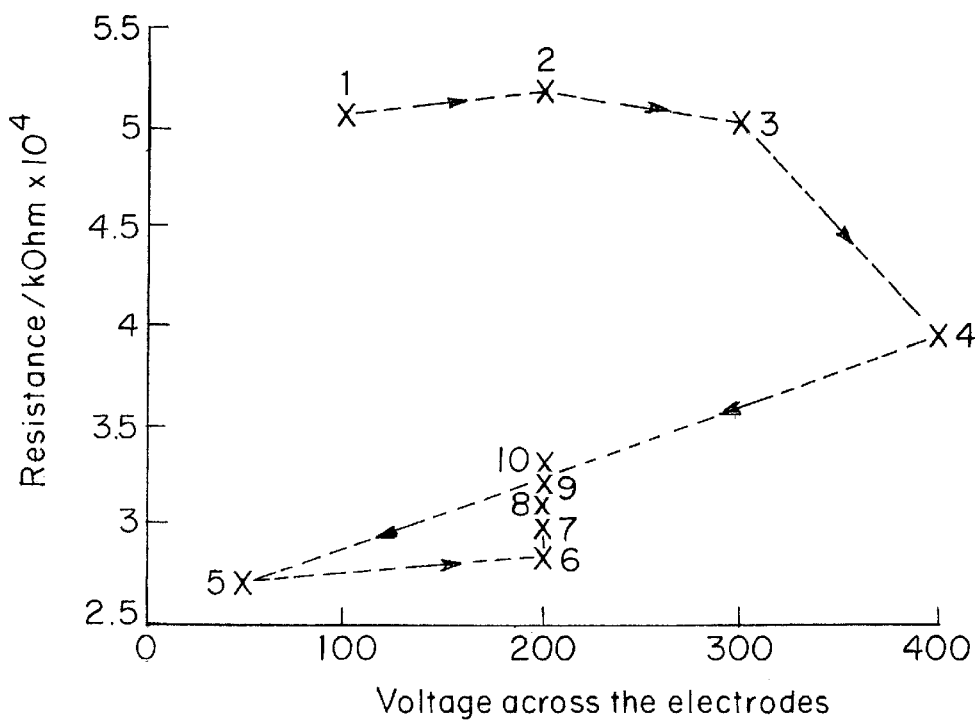
FIG. 8 is a plot of electrical resistance of epidermis of another subject versus pulse voltage applied to the epidermis by the method of the invention.

The results of the same type of experiment on a second subject are plotted in FIG. 8, in which the sequence of pulses is also labeled numerically as points 1 through 10. In this subject, no sensation was felt, but the change in the skin resistance strongly support the occurrence of electroporation. The repetition at 200 V did not cause any sensation but did cause reversible changes in the total resistance across the two skin sites (one not pulsed; see FIG. 1).

Figure 9:
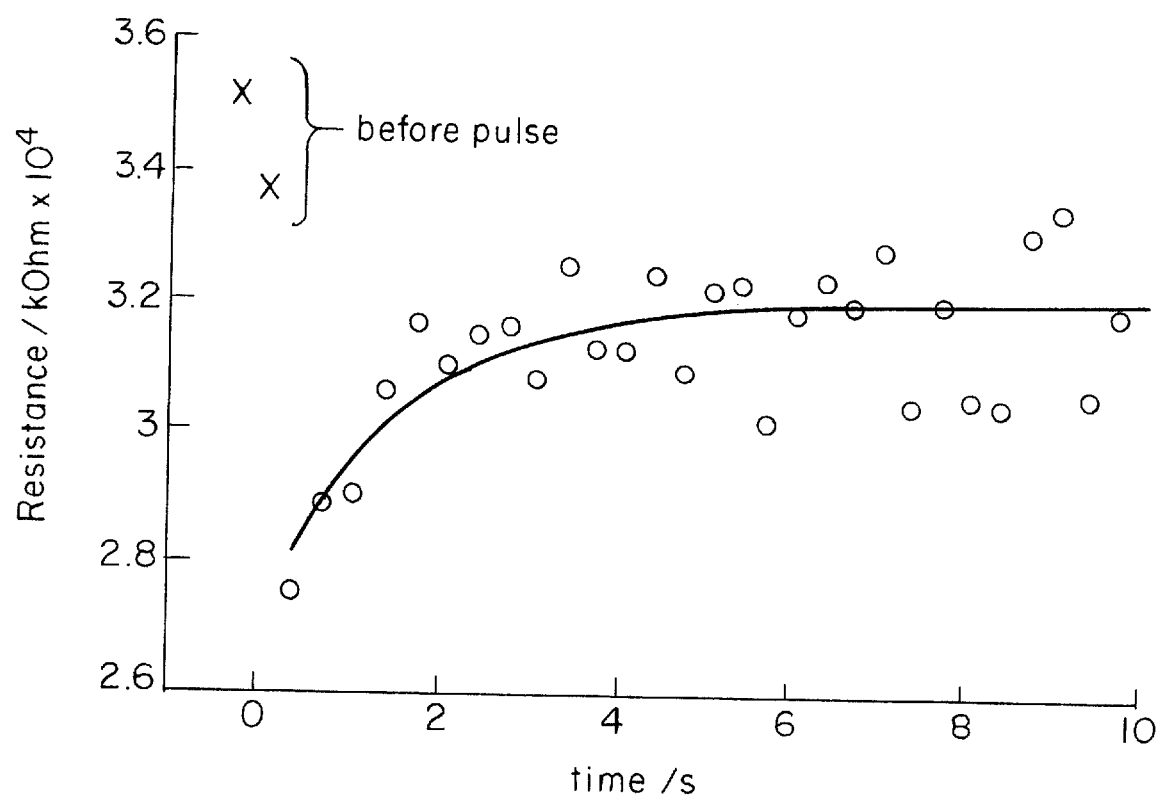
FIG. 9 is a plot of electrical resistance versus time following application of an electrical pulse to epidermis by the method of the invention.

FIG. 9 shows the time course of the resistance from a single 450 V pulse. A drop in resistance is evident as well as recovery within seconds to about 90% of the pre-pulse value. This too is consistent with electroporation.

Equivalents

Those skilled in the art will recognize, or be able to ascertain using no more than routine experimentation, many equivalents to specific embodiments of the invention described specifically herein. Such equivalents are intended to be encompassed in the scope of the following claims.

We claim:
1. An apparatus for electroporating a tissue, comprising:
   a) a perforate electrically insulating layer;
   b) at least one first external electrode contacting a first side of said perforate electrically insulating layer;
   c) a second electrode having a first surface and an opposite second surface, said second surface being located at a second side of said perforate electrically insulating layer, whereby an electric field extending between said first and second electrodes will preferentially extend through perforations of said electrically insulating layer, said electric field thereby causing electroporation of a tissue that is proximate to said first electrode and is partitioned from said electrically insulating layer and said second electrode by the first electrode; and d) means for conducting a fluid from the first surface of the second electrode to the second surface of said second electrode.

2. The apparatus of claim 1, wherein said first electrode is a plurality of first electrodes, whereby said first electrodes are electrically insulated from each other.

3. The apparatus of claim 1, wherein said first electrode is perforate.

4. The apparatus of claim 3, wherein at least a portion of perforations in said first electrode are substantially aligned with at least a portion of perforations of said electrically insulating layer.

5. The apparatus of claim 4, wherein said first electrode and said perforated electrically insulating layer are in contact with each other at said aligned perforations, whereby said aligned perforations can contain a material to be conducted into electroporated tissue at the first electrode.

6. The apparatus of claim 5, wherein said perforations of the first electrode have a larger diameter than diameter of perforations of the perforate electrically-insulating layer.

7. The apparatus of claim 5, further including a housing for containing a material to be directed into electroporated tissue at the first electrode, said housing defining an application opening at which the first electrode is located, said electrically insulating layer and said second electrode being contained by said housing and said first electrode.

8. The apparatus of claim 7 wherein said housing further defines an inlet for introduction of a material into said housing.

9. The apparatus of claim 8, further including a filter element located between said electrically insulating layer and said second electrode.

10. The apparatus of claim 9, further including an electrical resistance measurement means, comprising:

a) an electrical resistance measurement component;

b) a first electrical resistance measurement electrode connected to the electrical resistance measurement component and located at said housing; and c) a second electrical resistance measurement electrode for contact with the tissue and connected to said electrical resistance measurement component.

11. The apparatus of claim 9 further including means at said housing for pressurizing a material within said housing.

12. The apparatus of claim 11 wherein said means includes an ultrasound device.

13. The apparatus of claim 9 further including means for directing material into said housing.

14. The apparatus of claim 13 wherein said means includes a syringe at said housing.

15. The apparatus of claim 10, further including a switching means at said first and second electrodes for switching between application of an electric field and measurement of electrical resistance at the tissue.

16. An apparatus as in claim 1 wherein said first electrode is at least partially coated by a second electrically insulating layer.

17. A method for electroporating a tissue, comprising the steps of:

a) contacting at least one first electrode to the tissue;

b) forming an electric field between said first electrode and a second electrode that is partitioned from said first electrode by a nonconductive layer that contacts the first electrode, whereby said electric field preferentially extends around at least a portion of said insulating layer, the electric field thereby causing electroporation of tissue that is proximate to the first electrode; and c) forming a plurality of electric fields, each electric field being formed between a first electrode and the second electrode.

18. The method of claim 17 wherein said electric fields are formed sequentially to selectively designate at least one first electrode that is most proximate to a preferred location at said tissue for electroporation.

19. A method for causing iontophoresis in a tissue, comprising the steps of:

a) contacting a least one first electrode to the tissue;

b) forming an electric field between said first electrode and a second electrode that is partitioned from said first electrode by a nonconductive layer that contacts the first electrode, whereby said electric field preferentially extends around at least a portion of said insulating layer, the electric field thereby causing iontophoresis of tissue that is proximate to the first electrode; and c) directing a material from a first surface of the second electrode to a second surface of the second electrode and into iontophoresed tissue proximate to said first electrode.

20. A method of claim 19 wherein said electric field is formed by applying a voltage between said electrodes in a range of between about 0.1 volts and five volts.

* * * * *